United States Patent [19]

Wheldon

[11] Patent Number: 4,769,112
[45] Date of Patent: Sep. 6, 1988

[54] METHOD FOR REMOVING WATER FROM ETHANOL

[75] Inventor: Alfred G. Wheldon, Essex, Great Britain

[73] Assignee: United Distillers P.L.C., Scotland

[21] Appl. No.: 4,447

[22] Filed: Jan. 20, 1987

[30] Foreign Application Priority Data

Jan. 17, 1986 [GB] United Kingdom ................. 8601081

[51] Int. Cl.[4] ........................ B01D 3/14; B01D 11/04; B01D 15/00; C12P 7/06
[52] U.S. Cl. ........................................ 203/19; 203/26; 203/27; 203/41; 203/46; 203/49; 203/71; 203/DIG. 4; 203/DIG. 8; 203/DIG. 13; 426/494; 435/161; 568/916
[58] Field of Search .................. 203/49, 19, DIG. 13, 203/41, 74, 77, 84, 71, DIG. 8, DIG. 4, 26, 21, 27, 43–46; 435/161; 426/493, 494; 568/916, 918, 917

[56] References Cited

U.S. PATENT DOCUMENTS

| | | | |
|---|---|---|---|
| 4,273,621 | 6/1981 | Fornoff | 203/19 |
| 4,327,184 | 4/1982 | Johnson et al. | 203/DIG. 13 |
| 4,349,415 | 9/1982 | De Filippi et al. | 203/49 |
| 4,359,593 | 11/1982 | Feldman | 568/916 |
| 4,420,561 | 12/1983 | Chen | 435/161 |
| 4,465,875 | 8/1984 | Greenbank et al. | 568/916 |
| 4,487,614 | 12/1984 | Yon | 203/19 |
| 4,492,808 | 1/1985 | Hagen et al. | 568/918 |
| 4,522,920 | 6/1985 | Thorsson et al. | 435/161 |
| 4,556,460 | 12/1985 | Robertson et al. | 203/49 |

FOREIGN PATENT DOCUMENTS 0122539 4/1984 European Pat. Off. .
0158754 4/1984 European Pat. Off. .

Primary Examiner—Wilbur Bascomb
Attorney, Agent, or Firm—Sughrue, Mion, Zinn, Macpeak and Seas

[57] ABSTRACT

A method and apparatus for removing water from a liquid mixture of water and ethanol contacts it with liquid carbon dioxide so that the ethanol is preferentially transferred into solution, dries the solution using an adsorbent, and then recovers dry ethanol by distilling off the carbon dioxide. This process is particularly energy efficient especially when it includes a fermentation process to generate the ethanol and uses the carbon dioxide generated during the fermentation as the source of liquid carbon dioxide. In this case the method and apparatus provide an additional product of dry carbon dioxide.

20 Claims, 3 Drawing Sheets

METHOD FOR REMOVING WATER FROM ETHANOL

BACKGROUND OF THE INVENTION

This invention relates to a method and apparatus for removing water from a mixture containing both water and ethanol.

At present water is usually removed from such a mixture by distillation but ethanol forms a binary azeotrope with water and consequently, by using simple distillation techniques, it is impossible to remove all of the water. When producing a potable spirit azeotrope strength spirit is the maximum ethanol concentration that is produced. Water is removed from such a binary azeotrope to produce a substantially water-free ethanol for industrial use by adding a third component to produce a ternary system. Upon subsequent distillation of the ternary system substantially water-free ethanol is produced. To obtain substantially anhydrous ethanol using this technique requires a substantial quantity of energy and, in the past, a number of proposals have been made to remove the water more efficiently. For example, it is known to treat an azeotrope mixture with a desiccant such as fused sodium or potassium acetate and thereby remove water from such a mixture. It is also known to use a molecular sieve dryer operating in either the liquid or the vapour phase to remove the last remaining traces of water from substantially water-free ethanol but, in general, the use of a molecular sieve has been confined to such a polishing role.

In addition to these conventional techniques specific proposals are described in U.S. Pat. Nos. 3,132,079, 4,273,621 and EP-A-No. 0158754 involving the use of a molecular sieve to remove water from an azeotrope vapour resulting from distillation and containing an organic liquid and water. In the first of these a method is discussed in which a molecular sieve is used to adsorb water from a vapour phase azeotrope mixture of water and isopropanol. To regenerate the molecular sieve some of the water-free isopropanol so produced is heated and passed through the molecular sieve in the reverse direction to remove water from the water saturated molecular sieve. This wet isopropanol is then returned to the distillation system. This conserves the isopropanol but the system is inefficient and uses a great deal of energy firstly in the distillation of the mixture to obtain the vapour phase azeotrope and secondly to heat the dry isopropanol so produced and use this to regenerate the molecular sieve. This results in wetting the isopropanol again and hence reducing the yield of dry isopropanol whilst, at the same time, requiring the use of still further energy to redistil the re-wetted isopropanol.

In the second of these proposals, a system for removing water from a vapour phase ethanol/water azeotrope is described in which an ethanol/water mixture is subjected to high pressure distillation at a pressure of 7.5 bar. The resulting vapour phase azeotrope is then diluted with a carrier gas consisting of carbon dioxide or nitrogen and passed through a molecular sieve to remove the water vapour. The ethanol is allowed to condense out and the carrier gas is used in the regeneration of the water saturated molecular sieve. By careful choice of operating temperatures and pressures and also using the heat of adsorption and desorption it is possible to use very little energy for the removal of the water from the vapour phase azeotrope but, of course, the high pressure distillation part of the process does require a considerable amount of energy. Moreover, this system is entirely concerned with the removal of water from the vapour and not only relies on it being a vapour but on it being a vapour resulting from a high pressure distillation system. This system could not be applied to a liquid feed stock unless that liquid feed stock was vaporized initially and this would also require considerable quantities of energy.

In the third of these a process is described in which a carbon molecular sieve is used to remove water from an ethanol/water azeotrope vapour and it is postulated that such molecular sieves could also be used to remove water from ethanol in the liquid phase.

Other proposals have been made, for example in EP-A-No. 0122539 and U.S. Pat. No. 4,420,561 to adsorb ethanol onto a molecular sieve material to remove it from an ethanol/water mixture and then recover the ethanol upon regenerating the molecular sieve material.

SUMMARY OF THE INVENTION

According to a first aspect of this invention a method of removing water from a mixture containing water and ethanol comprises the steps of:

(a) contacting a liquid ethanol water mixture with liquid carbon dioxide so that the ethanol is preferentially transferred from the mixture into solution with the liquid carbon dioxide to increase the ratio of ethanol to water in the liquid carbon dioxide;

(b) supplying heat to the mixture containing ethanol and carbon dioxide to vaporize it and thereby increase the proportion of ethanol in the mixture and concentrate it;

(c) scrubbing the vapour evolved from step (b) with the mixture fed to step (b) to remove substantially all of the ethanol from the vapour evolved in step (b);

(d) condensing the evaporated carbon dioxide vapour and recycling the reformed liquid carbon dioxide to return it to the contaction step (a);

(e) continuing the recycling of the reformed liquid carbon dioxide to increase the concentration of ethanol and so produce a concentrated mixture;

(f) drying the combined mixture resulting from step (a) or the concentrated mixture resulting from step (e) by a process including contacting the mixture with an adsorbent which adsorbs substantially all the water from it;

(g) feeding the concentrated dry mixture containing ethanol and carbon dioxide to a distillation column which is cooled at the top and heated at the base to recover substantially water free ethanol at the base.

According to a second aspect of this invention a plant for removing water from a mixture containing water and ethanol comprises:

a contaction column having a first inlet for the mixture containing ethanol and water, a second inlet for liquid carbon dioxide below the first inlet, a first outlet for the stripped mixture below the second inlet, and a second outlet for a solution of ethanol and liquid carbon dioxide above the first inlet;

first heat exchange means having a liquid inlet, a liquid outlet and a vapour outlet;

second heat exchange means having a vapour inlet and a liquid outlet;

a tailing column having a liquid inlet and outlet and a vapour inlet and outlet, the vapour outlet from the tailing column being connected to the vapour inlet of the second heat exchange means, the liquid outlet of the tailing column being connected to the liquid inlet of the first heat exchange means and the vapour outlet of the first heat exchange means being connected to the vapour inlet of the tailing column;

means connected between the liquid outlet of the second heat exchange means and the second inlet of the liquid-liquid contaction column;

a distillation column having a liquid inlet; and, a dryer including an adsorbent material, the dryer having an inlet and an outlet and being connected in series between the second outlet of the contaction column and the liquid inlet of the tailing column or connected between the liquid outlet of the first heat exchange means and the liquid inlet of the distillation column; the distillation column having a vapour outlet located at its top and a liquid outlet at its base from which water free ethanol is recovered.

Preferably the ethanol content of the ethanol/water mixture is as high as possible and is at least 40% or 60% w/w and more preferably at least 70% w/w. It is especially preferred that the ethanol content of the mixture is substantially 80% w/w. Preferably the solution of ethanol and liquid carbon dioxide leaving the contaction step has its ratio of ethanol to water increased to at least 9:1 during the contaction step. This reduces the amount of water to be removed by the dryer and hence reduces the energy required to regenerate the molecular sieve. Preferably the concentration of ethanol in the substantially water-free mixture is increased in step (e) until it is present at at least 25% w/w.

Typically a fermented wash has an ethanol content of between 6% and 12% w/w. Before such a wash can economically have water removed from it by a method and apparatus in accordance with this invention the fermented wash must be subjected to an initial concentration process. Similarly the product obtained by the industrial synthesis of ethanol is an ethanol water mixture having a low concentration of ethanol. Accordingly such mixtures should also be subject to an initial concentration process.

The initial concentration process may have the form of a simple distillation carried out in a wash still which strips substantially all of the ethanol from the fermented wash or it may include some rectification and reflux stages to increase the ethanol content to a higher level and typically to between 70 and 80% w/w of ethanol. When the ethanol is obtained by fermentation it is also possible to provide a continuous fermentation and primary distillation step in which a continuous fermentation process is employed with a substrate to be fermented being introduced continuously into a fermenter and the resulting fermented wash being passed through a distillation column providing an output of between 30% and 40% ethanol w/w. A part of the stripped wash is then returned to the fermenter and the remainder is concentrated and discharged as stillage.

The energy costs for an initial concentration step using conventional distillation techniques or a continuous fermentation distillation process are not great. The energy costs of conventional distillation processes only increase substantially when they are used to increase the ethanol concentration to more than 80% w/w, as shown in Table 1 below.

TABLE 1

| Energy required to increase ethanol concentration from x% to y% by weight | | |
|---|---|---|
| x | y | KJ/Kg |
| 10 | 60 | 3,100 |
| 10 | 70 | 3,200 |
| 10 | 80 | 3,300 |
| 10 | 90 | 3,800 |
| 10 | 93 | 4,400 |
| 10 | 95 | 6,300 |

By connecting the dryer in series between the liquid outlet of the first heat exchange means and the liquid inlet of the distillation column and hence carrying out the drying step (f) on the concentrated mixture resulting from step (e) less water has to be removed by the dryer. This results from the mixture of ethanol and carbon dioxide being concentrated at this point. As a result of this the size and capacity of the dryers can be reduced by about ten percent. However, connecting the dryer in series between the second outlet of the contaction column and the liquid inlet of the tailing column and hence carrying out the drying step (f) on the mixture resulting from the contaction step (a) has the advantage that all the apparatus downstream of the dryers can then be made of mild steel instead of stainless steel and this reduces considerably the cost of the plant.

Preferably the means connected between the liquid outlet of the second heat exchange means and the second inlet of the liquid-liquid contaction column include a hold-up tank in which the condensed liquid carbon dioxide collects and from which the condensed liquid carbon dioxide is taken to the second inlet of the liquid-liquid contaction column. A cooler may be connected between the outlet of the hold-up tank and the second inlet of the liquid-liquid contaction column to ensure that the liquid carbon dioxide is at a temperature below its equilibrium point at the pressure subsisting in the contaction column. This ensures that the carbon dioxide remains in a liquid state during its flow through the liquid-liquid contaction column. The liquid-liquid contaction column may be, for example, a sieve plate column, a packed column, a bubble-cap column, a falling film column, a spray column or a disc and doughnut column.

It is preferred that the contaction step between the mixture containing ethanol and water and the liquid carbon dioxide is carried out at a temperature above 10° C. Above 10° C. there is sufficient difference in density between the ethanol and water and the liquid carbon dioxide to enable a very effective contaction and separation to take place. Another advantage of working above this temperature is that formation of carbon dioxide hydrate $CO_2.8H_2O$ is prevented. This carbon dioxide hydrate is a solid which can inhibit the flow in the contaction column.

The first and second heat exchange means may be opposite sides of a common heat exchanger. In this case a carbon dioxide vapour compressor is connected between the vapour outlet of the tailing column and the vapour inlet of the second heat exchange means. With this arrangement the heat of vaporisation required to vaporise liquid carbon dioxide in the first heat exchange means is provided mainly by the heat of liquefaction of carbon dioxide vapour evolved in the second heat exchange means as described fully in our earlier specification GB-A-No. 1557123. This arrangement is particularly energy efficient but the temperatures subsisting in the first and second heat exchange means are naturally linked together taking into account the capacity and performance of the compressor.

Alternatively the first and second heat exchange means may be formed by separate first and second heat exchangers each having a primary path for a warm vapour medium to be cooled and liquefied and a secondary path for a cool liquid medium to be warmed and vaporized. In this case preferably the primary path of the first heat exchanger is connected in a loop with the secondary path of the second heat exchanger with a compressor on one side of the loop and an expansion valve on the other side of the loop to provide a heat pump system with a working fluid such as an halogenated hydrocarbon, for example dichlorodifluoromethane. In this case it is the heat of liquefaction of the working fluid which provides the heat required to evaporate the carbon dioxide vapour from the secondary path of the first heat exchanger and the cooling caused by evaporation of the working fluid at a lower pressure and therefore temperature which condenses the carbon dioxide vapour in the primary path of the second heat exchanger. This system may use a little more energy than the first system described although it is still energy efficient but this extra energy usage is offset by the advantages gained by being able to decouple the temperatures of the heat exchange surfaces in the first and second heat exchangers.

When the apparatus includes a fermenter it is preferred that the carbon dioxide produced during the fermentation of, for example, a cereal product, is used to provide the liquid carbon dioxide used in accordance with this invention, and it is preferred that dry substantially pure carbon dioxide is produced as an additional product of this invention by recovering it as a top product from the distillation column producing dry ethanol as its bottom product. In this case a carbon dioxide outlet from the fermenter is fed to a carbon dioxide compressor and then the condensed carbon dioxide is fed to the second inlet of the contaction column.

The dryer may also include an initial pervaporation dryer in which water is removed using a preferentially permeable membrane. However it is preferred that the dryer consists solely of the adsorbent material. It is preferred that the adsorbent material has a pore aperture size of substantially 3 Angstroms (0.3 nm). Also it is preferred that the adsorbent material is a crystalline zeolite.

Preferably the dryer consists of at least two and preferably four chambers arranged in parallel so that the full flow of the combined mixture leaving the contaction column or the concentrated mixture leaving the liquid outlet of the first heat exchanger passes through one of the chambers to have the water removed from it whilst the adsorbent material in the other, or others, of the chambers is regenerated. The recompressed and recondensed carbon dioxide may be used to flush the ethanol rich carbon dioxide from the dryer before its regeneration.

Preferably the outlet of the compressor which compresses the carbon dioxide from the fermenter is fed to a heat exchanger in which it is cooled. Heat from the compressed carbon dioxide gas is used to heat air in the heat exchanger and this hot air is then used to regenerate the adsorbent material in the dryer. The compressed carbon dioxide is also passed through a cooler before being fed to the contaction column.

Preferably the raffinate leaving the second outlet of the liquid-liquid contaction column is fed to a raffinate degasser which separates the carbon dioxide from the spent liquid. This carbon dioxide is preferably introduced into the flow of carbon dioxide leaving the fermenter and is then compressed and recirculated. Preferably the degassed raffinate is returned to the fermenter to be used again in the fermentation.

Where the initial mixture containing ethanol and water is produced by a fermentation process the mixture typically includes congeners such as fusel oils and higher alcohols. The congeners tend to carry through the method and apparatus in accordance with this invention and so are present in the final anhydrous ethanol output. Where the anhydrous ethanol product produced by the method and apparatus in accordance with this invention is intended to be used as a liquid fuel, or a liquid fuel additive, the presence of the congeners and is irrelevant and thus the product obtained from the base of the distillation column can be used directly for such purposes. However, where the anhydrous ethanol product is required for potable purposes or where it is required to obtain substantially pure ethanol the output obtained from the base of the stripping column is preferably subjected to a fractional distillation process to separate the ethanol from the congeners. Substantially pure anhydrous ethanol can be readily separated from the congeners by this fractional distillation process since water is absent. When this further distillation step is carried out in a single fractionating column there is inevitably some carry over of the higher or lower boiling point fractions. For some purposes such as for use in the fortification of wines this may be satisfactory. However, it is preferred that separate topping and tailing columns are used to provide substantially pure anhydrous ethanol.

BRIEF DESCRIPTION OF THE DRAWINGS

Examples of a method and apparatus in accordance with the present invention will now be described with reference to the accompanying drawings, in which.

DESCRIPTION OF PREFERRED EXAMPLE

Figure 1:
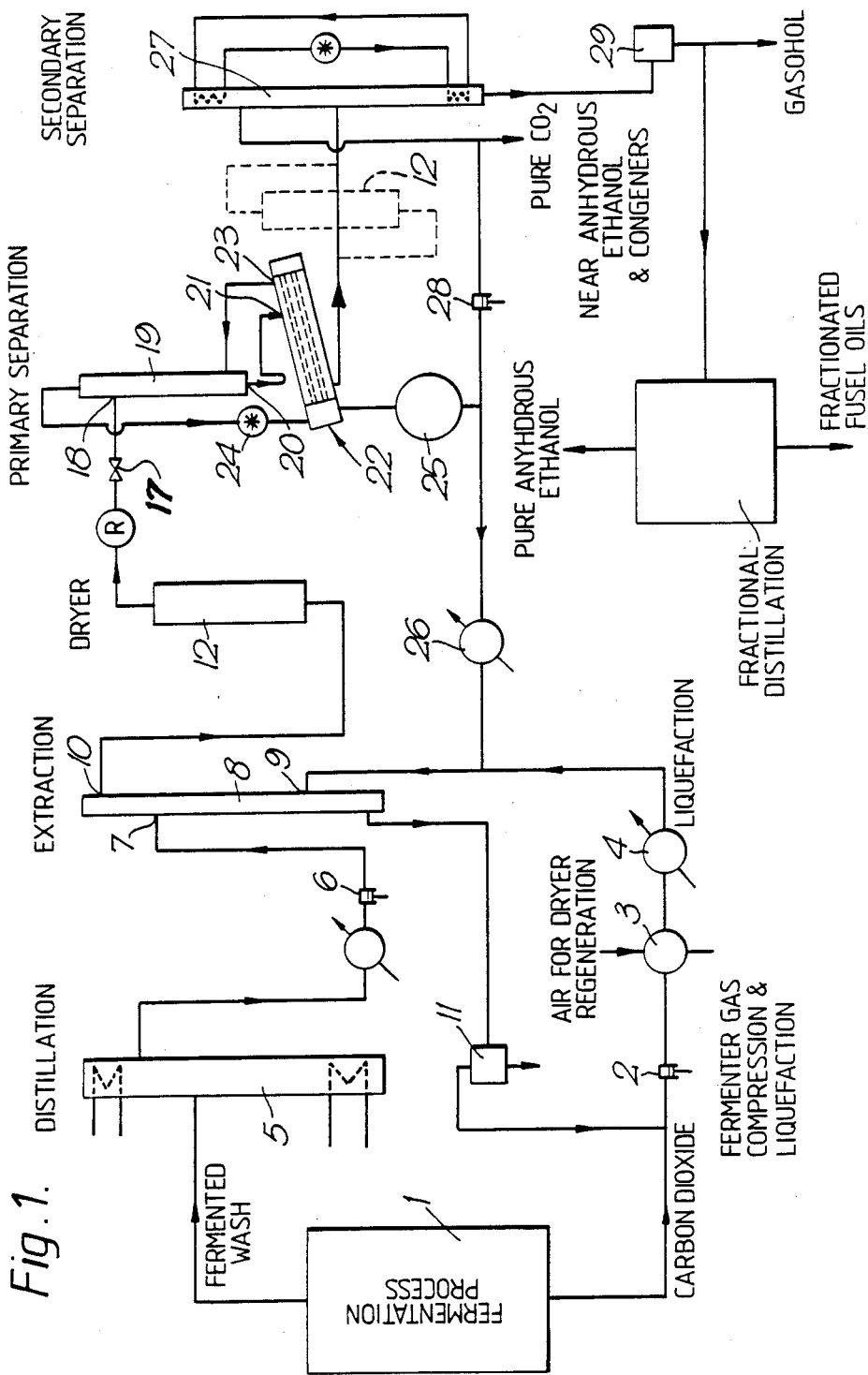
FIG. 1 is a diagram of a first example of the apparatus.

A carbohydrate feedstock is fermented by yeast in a fermenter 1 to a product containing up to 12% w/w ethanol but more typically 6% w/w ethanol. The carbon dioxide evolved from the fermentation process is compressed in a compressor 2 and then cooled in a heat exchanger 3 followed by a cooler 4 to liquefy it. This fermented wash is then distilled in a simple distillation plant 5 to produce an ethanol water mixture which typically contains about 80% by weight of ethanol. This mixture is pumped by a pump 6 into a first inlet 7 of a contaction column 8. Contaction column 8 is a sieve plate column having twenty-five plates made from stainless steel. The contaction column 8 typically operates at a pressure of 59 bar and at a temperature of 15° C. Liquid carbon dioxide from the cooler 4 downstream of the compressor 2 is introduced into a second inlet 9 located at the base of the contaction column 8 and passes upwards through the contaction column 8 in counter-current to the ethanol water mixture.

Ethanol and the congeners are preferentially taken into solution with the liquid carbon dioxide and a carbon dioxide solution rich in ethanol leaves a first outlet 10 in the top of the contaction column 8. The typical composition at this point is 90% w/w carbon dioxide, 9.3% w/w ethanol plus congeners, and 0.7% w/w water. The raffinate from the contaction column 8 is essentially water with small amounts of alcohol and carbon dioxide in solution. This is depressurised on entry to a vapour separator 11 from which the carbon dioxide is returned to the process via the fermentation gas compressor 2. The aqueous solution is returned to either the primary distillation or to the fermentation system.

Figure 3:
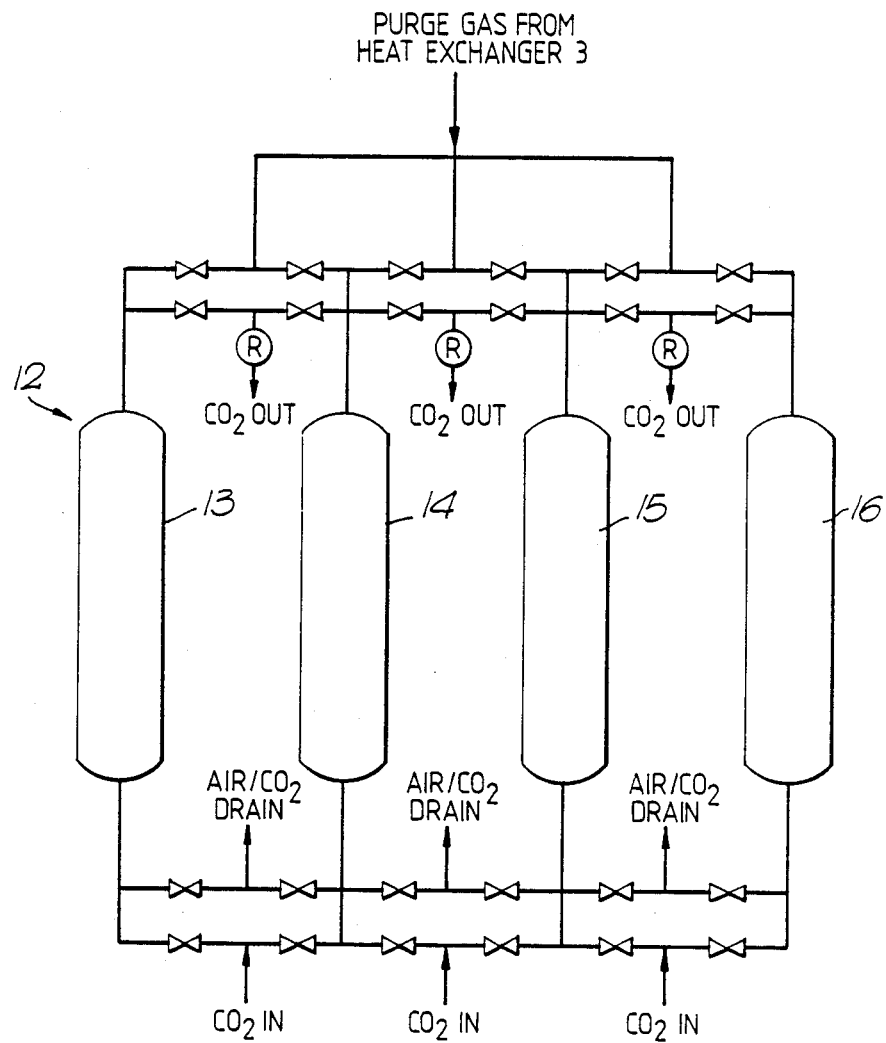
FIG. 3 is a diagram of the dryer.

The first outlet 10 at the top of the contaction column 8 is connected to a dryer system 12 shown in more detail in FIG. 3, consisting of four molecular sieve dryers 13, 14, 15 and 16 connected in parallel. The dryers 13-16 are all packed with a crystalline zeolite having a nominal pore aperture size of 3 Angstroms (0.3 nm) such as type 3A manufactured by Laporte Industries plc of Luton, Bedfordshire. Typically the crystalline zeolite is present as 1 to 2 mm spheres. The dryers typically operate at a temperature of 15° C. and at an inlet pressure of 59 bar. The molecular sieve material adsorbs water to the extent of about 20% of its own weight before it requires regeneration.

At any instant only one of the dryers 13-16 is connected in series with the flow of carbon dioxide to adsorb water from the solution of ethanol and carbon dioxide. The other dryers are being regenerated or in a regenerated condition standing by to take over. The outlet from the dryer system 12 leads, via an analyser R to a flow control valve 17 and thence to an inlet 18 to a tailing column 19. The analyser R monitors the flow for the presence of water and, upon detection of water, changes from one to the other of the molecular sieve dryers 13-16.

The tailing column 19 is a packed column packed with half inch (12.5 mm) mild steel pall rings which typically operates at a temperature of 18° C. and a pressure of 54 bar. The carbon dioxide ethanol solution then leaves a liquid outlet 20 in the base of the column 19 and is led to a liquid inlet 21 in the shell side of an inclined shell and tube heat exchanger 22. The tailing column 19 and the heat exchanger 22 form a simple distillative system in which the ethanol concentration is increased from approximately 9% w/w to approximately 30% w/w.

Typically the heat exchanger 22 is also made from mild steel. The carbon dioxide and ethanol solution is evaporated in the shell side of the heat exchanger 22 and the resulting vapour leaves a vapour outlet 23 in the shell side of the heat exchanger 22 and is taken to a vapour inlet 23 of the tailing column 19. In the tailing column 19 the flow of liquid carbon dioxide and ethanol scrubs the vapour leaving the shell side of the heat exchanger 22 to reduce the ethanol content so that the vapour leaving a vapour outlet in the top of the tailing column 19 contains substantially only carbon dioxide. This carbon dioxide vapour is fed to a compressor 24 which is typically a single stage reciprocating compressor. The compressed gas is then fed into the tube side of the heat exchanger 22. The carbon dioxide vapour is heated during its recompression in compressor 24 and thus, when the recompressed carbon dioxide vapour is reintroduced into the tube side of the heat exchanger 22 it gives up both sensible and latent heat to cause evaporation of carbon dioxide and ethanol solution in the shell side of the heat exchanger 22. Meanwhile the compressed carbon dioxide vapour recondenses to form liquid carbon dioxide which leaves the tube side of the heat exchanger 22 and is received in a hold-up tank 25. The hold-up tank 25 typically operates at a pressure of the order of 67 bar and at a temperature of around 27° C.

Liquid carbon dioxide from the hold-up tank 25 is taken via the heat exchanger 26 which cools the carbon dioxide before introducing it through the second inlet 9 in the base of the contaction column 8. The degree of cooling exerted by the cooler 4 and by the heat exchanger 26 is controlled by temperature controllers to ensure that the carbon dioxide introduced into the contaction column 8 is below its boiling point and at the required extraction temperature.

A liquid outlet from the shell side of the heat exchanger 22 feeds the ethanol carbon dioxide solution which is rich in ethanol and typically has an ethanol concentration of around 30% w/w into a distillation column 27. The distillation column 27 is typically a packed column packed with quarter inch (6 mm) mild steel Raschig or Lessing rings having a heat pump system 28 connected to its base and top to provide reflux and boil-up. The heat pump system 28 typically uses an halogenated hydrocarbon such as dichlorodifluoromethane. In this secondary system carbon dioxide of high purity is obtained from the head of the distillation column 27 and ethanol containing less than 0.5% water w/w is obtained from the base. The pressure of the secondary system is generally less than that of the primary system since this facilitates flow from the primary to secondary system. The ease of separation of the ethanol plus congeners and the carbon dixoide is also improved at the lower pressures.

The high purity carbon dioxide from the head of the column 27 is suitable for sale for most purposes without further purification treatment. A proportion is recycled to the process by means of a pump 28.

The substantially anhydrous mixture of ethanol and congeners is expanded from the base of the column 27 to a vapour/liquid separator 29. The liquid phase from this separator is passed to a fractional distillative unit which produces pure anhydrous ethanol and, fractionated fusel oils.

In a modification of this example the dryer 12 is connected in series between the liquid outlet from the shell side of the heat exchanger 22 and the distillation column 27 as shown by dotted lines in FIG. 1. In this modification the first outlet 10 in the top of the contaction column 8 is connected directly to the inlet 18 of the tailing column 19. In this case, since the solution containing ethanol is more concentrated the capacity of each of the dryers 13-16 can be reduced by about 10%. Also, since the pressure is lower at this point the dryers can be less robustly constructed. However, with the dryer system 12 located in this position all of the heat exchanger 22 and tailing column 19 have to be made of stainless steel.

To regenerate the dryer system 12 firstly the dryer to be regenerated, say dryer 13, is isolated from the flow of carbon dioxide solution leaving the contaction column 8 and this flow is fed via the dryer 14. All of the liquid from the dryer system 12 is drained and then it is connected to regenerated dryer 16 to pressurise this with carbon dioxide. The dryer system 12 is then depressurised. Air which has been heated in the heat exchanger 3 is fed to the dryer system 12 to desorb and flush out the water. The flow of air may be heated further in a booster heater (not shown) if sufficient heat is generated by the compression of carbon dioxide. The easy draining of the liquid carbon dioxide/ethanol/water mixture from the bed is important as it results in negligible retention of ethanol in the bed at the commencement of the regeneration. After all the water has been removed the flow of hot air is stopped and then the bed of crystalline zeolite is cooled by flushing with cool air. The cool air after becoming heated by the hot bed may be used to start regeneration of the next dryer 14. After the dryer system 12 is cool it is flushed with carbon dioxide from the next dryer 13 to be regenerated to remove the air and then repressurized to its normal operating pressure. It then stands by to receive the carbon dioxide solution. This process is repeated on each dryer in turn when it requires regeneration. The use of a multiplicity of dryers enables the process to proceed without interruption.

Figure 2:
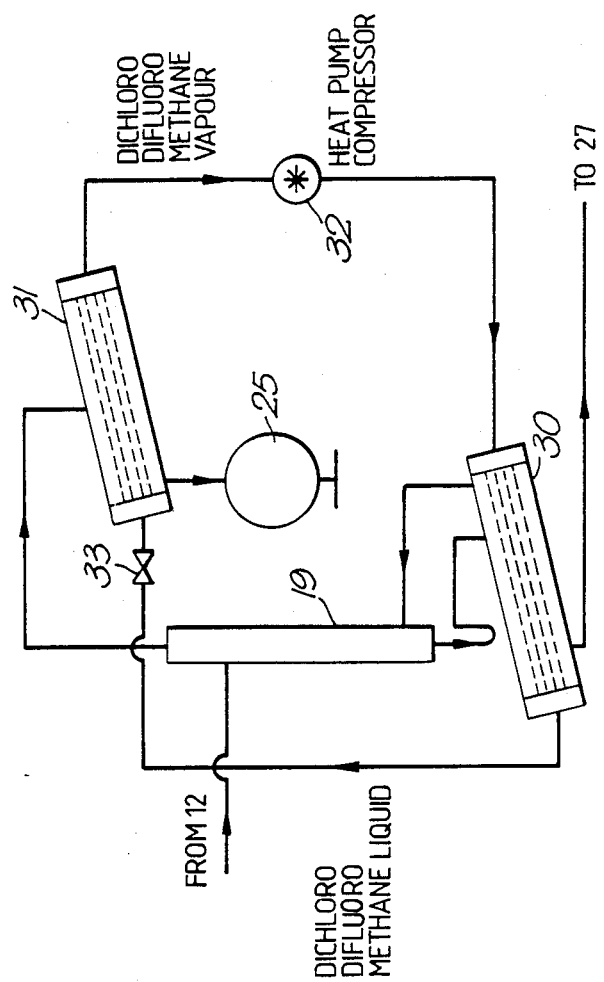
FIG. 2 is a diagram of part of a second example of the apparatus.

The second example is identical to the first example with the exception of the parts shown in FIG. 2 which are used instead of the heat exchanger 22 and compressor 24. In the second example two separate heat exchangers 30 and 31 are provided and these are connected in a closed loop with an halogenated hydrocarbon heat pump system. The heat pump comprises a compressor 32 and an expansion valve 33 and the working fluid is typically dichlorodifluoromethane. This is compressed by the compressor 32 and the heat liberated by the condensation of the working fluid in the heat exchanger 30 provides the heat required to evaporate carbon dioxide from the mixture leaving the molecular sieve dryer 12. Evaporation of the working fluid at a lower pressure and therefore temperature after passing through the valve 33 results in condensation of the carbon dioxide vapour in the heat exchanger 31. This system has the advantage that the temperatures of the heat exchangers 30 and 31 and hence of the heat exchange surfaces used to provide heat to the carbon dioxide ethanol mixture and take heat from the carbon dioxide vapour are independent of one another.

I claim:
1. A method of removing water from a mixture containing water and ethanol comprising the steps of:
    (a) contacting a liquid ethanol water mixture with liquid carbon dioxide as a contaction step whereby the ethanol is preferentially transferred from said liquid ethanol water mixture into solution with said liquid carbon dioxide to increase the ratio of ethanol to water in said liquid carbon dioxide and provide a first fraction comprising ethanol/water and a second fraction comprising ethanol/water/carbon dioxide;
    (b) drying said second fraction comprising ethanol/water/carbon dioxide resulting from step (a) to produce a dry mixture comprising ethanol and carbon dioxide by a process including contacting said combined mixture with an absorbent which adsorbs substantially all of said water from it;
    (c) supplying heat to said dry mixture comprising ethanol and carbon dioxide to cause volatilization of a fraction rich in carbon dioxide and removing said carbon dioxide rich fraction to thereby increase the proportion of ethanol in the remaining dry mixture;
    (d) scrubbing the carbon dioxide rich vapour evolved in step (c) with said dry mixture to remove substantially all of said ethanol from the carbon dioxide rich vapour evolved in step (c) thereby producing a carbon dioxide fraction;
    (e) condensing said carbon dioxide fraction to reform liquid carbon dioxide and recycling said reformed liquid carbon dioxide to contaction step (a);
    (f) continuing said recycling of the reformed liquid carbon dioxide to increase the concentration of ethanol and so produce a concentrated dry mixture;
    (g) feeding said concentrated dry mixture containing ethanol and carbon dioxide to a distillation column having a cooled top and a heated bottom and recovering substantially water free ethanol from said bottom of said distillation column.

2. A method according to claim 1, in which said combined mixture of ethanol and liquid carbon dixoide leaving said contaction step (a) has its ratio of ethanol to water increased to at least 9:1 during said contaction step.

3. A method according to claim 1, in which the concentration of ethanol in said concentrated dry mixture is increased in step (f) until it is present at at least 25% w/w.

4. A method according to claim 1, in which said liquid ethanol water mixture is subjected to an initial concentration process before said contaction step (a).

5. A method according to claim 1, in which said liquid ethanol water mixture is obtained by a continuous fermentation and primary distillation step in which a continuous fermentation process is employed with a substrate to be fermented being introduced continuously into a fermenter and a fermented wash resulting from such fermentation being distilled to provide an output liquid ethanol water mixture containing between 30% and 40% ethanol w/w.

6. A method according to claim 1, in which said adsorbent is a crystalline zeolite having a pore aperture size of substantially 3 Angstroms (0.3 nm).

7. A method according to claim 1, in which said liquid ethanol water mixture is produced by fermentation and carbon dioxide produced during said fermentation is used to provide said liquid carbon dioxide and in which dry substantially pure carbon dioxide is produced as an additional product by recovering it as a product from said top of said distillation column in step (g).

8. A method according to claim 6, in which said liquid ethanol water mixture is produced by fermentation and carbon dioxide produced during said fermentation is used to provide said liquid carbon dioxide and in which dry substantially pure carbon dioxide is produced as an additional product by recovering it as a product from said top of said distillation column in step (g).

9. A method according to claim 1, wherein said mixture containing water and ethanol is produced by fermentation, and wherein carbon dioxide produced in said fermentation is used as a liquid carbon dioxide in step (a), and wherein said adsorbent which adsorbs substantially all of said water from said ethanol/water/carbon dioxide mixture is regenerated by heating, and the heat for regeneration of said adsorbent is provided by compressing carbon dioxide produced by fermentation to said liquid carbon dioxide for contacting said liquid ethanol/water mixture.

10. A method according to claim 1, in which said substantially water-free ethanol obtained from said bottom of said distillation column is subjected to a fractional distillation process to separate ethanol and congeners and provide a substantially pure anhydrous ethanol product.

11. A method of removing water from a mixture containing water and ethanol comprising the steps of:
  (a) contacting a liquid ethanol water mixture with liquid carbon dioxide as a contaction step whereby ethanol is preferentially transferred from said liquid ethanol water mixture into solution with said liquid carbon dioxide to increase the ratio of ethanol to water in said liquid carbon dioxide and provide a first fraction comprising ethanol/water and a second fraction comprising ethanol/water/carbon dioxide;
  (b) supplying heat to said second fraction comprising ethanol/water/carbon dioxide to cause volatilization of a fraction rich in carbon dioxide and removing said carbon dioxide rich fraction to thereby increase the proportion of ethanol in the remaining fraction;
  (c) scrubbing the carbon dioxide rich vapour evolved in step (b) to remove substantially all of said ethanol from said carbon dioxide rich vapour evolved in step (b) thereby producing a carbon dioxide fraction;
  (d) condensing said carbon dioxide fraction to reform liquid carbon dioxide and recycling said reformed liquid carbon dioxide to contaction step (a);
  (e) continuing said recycling of the reformed liquid carbon dioxide to increase the concentration of ethanol and so produce a concentrated mixture;
  (f) drying said second fraction comprising ethanol/water/carbon dioxide resulting from step (e) to produce a concentrated dry mixture comprising ethanol and carbon dioxide by a process including contacting said combined mixture with an adsorbent which adsorbs substantially all of said water from it;
  (g) feeding said concentrated dry mixture containing ethanol and carbon dioxide to a distillation column having a cooled top and a heated bottom and recovering substantially water free ethanol from said bottom of said distillation column.

12. A method according to claim 11 in which said combined mixture of ethanol and liquid carbon dioxide leaving said contaction step (a) has its ratio of ethanol to water increased to at least 9:1 during said contaction step.

13. A method according to claim 11, in which the concentration of ethanol in said concentrated mixture is increased in step (e) until it is present at at least 25% w/w.

14. A method according to claim 11, in which said liquid ethanol water mixture is subjected to an initial concentration process before said contaction step (a).

15. A method according to claim 11, in which said liquid ethanol water mixture is obtained by a continuous fermentation and primary distillation step in which a continuous fermentation process is employed with a substrate to be fermented being introduced continuously into a fermenter and a fermented wash resulting from such fermentation being distilled to provide an output liquid ethanol water mixture containing between 30% and 40% ethanol w/w.

16. A method according to claim 11, in which said adsorbent is a crystalline zeolite having a pore aperture size of substantially 3 Angstroms (0.3 nm).

17. A method according to claim 11, in which said liquid ethanol water mixture is produced by fermentation and carbon dioxide produced during said fermentation is used to provide said liquid carbon dioxide, and in which dry substantially pure carbon dioxide is produced as an additional product by recovering it as a product from said top of said distillation column in step (g).

18. A method according to claim 11, in which said liquid ethanol water mixture is produced by fermentation and carbon dioxide produced during said fermentation is used to provide said liquid carbon dioxide, and in which dry substantially pure carbon dioxide is produced as an additional product by recovering it as a product from said top of said distillation column in step (g).

19. A method according to claim 11, wherein said mixture containing water and ethanol is produced by fermentation, and wherein carbon dioxide produced in said fermentation is used as a liquid carbon dioxide in step (a), and wherein said adsorbent which adsorbs substantially all of said water from said ethanol/water/carbon dioxide mixture is regenerated by heating, and the heat for regeneration of said adsorbent is provided by compressing carbon dioxide produced by fermentation to said liquid carbon dioxide for contacting said liquid ethanol/water mixture.

20. A method according to claim 11, in which said substantially water-free ethanol obtained from said bottom of said distillation column is subjected to a fractional distillation process to separate ethanol and congeners and provide substantially pure anhydrous ethanol product.

* * * * *